United States Patent [19]

Shigematsu et al.

[11] 4,226,855
[45] Oct. 7, 1980

[54] PLANT VIRAL DISEASE PREVENTIVE ALGINATE CONTAINING COMPOSITIONS

[75] Inventors: Taichiro Shigematsu, Machida; Tetsuya Shibahara; Hiroshi Kasugai, both of Yokohama; Tetsuo Nakajima, Kawasaki; Shozo Motojima, Hatano, all of Japan

[73] Assignee: Mitsubishi Chemical Industries Ltd., Tokyo, Japan

[21] Appl. No.: 858,791

[22] Filed: Dec. 8, 1977

[30] Foreign Application Priority Data

Dec. 16, 1976 [JP] Japan ................................ 51-151406
Dec. 17, 1976 [JP] Japan ................................ 51-151631

[51] Int. Cl.$^2$ .............................................. A61K 27/00
[52] U.S. Cl. ..................................... 424/177; 424/180; 536/1; 536/3
[58] Field of Search ................. 424/180, 177; 536/3, 536/1; 531/1

[56] References Cited

U.S. PATENT DOCUMENTS

| | | | |
|---|---|---|---|
| 2,426,125 | 8/1947 | Steiner | 536/3 |
| 3,772,266 | 11/1973 | Pettitt et al. | 536/3 |
| 3,891,756 | 6/1975 | Kasugai et al. | 424/180 |
| 3,948,881 | 4/1976 | Strong | 536/3 |

FOREIGN PATENT DOCUMENTS 48-18446  6/1973  Japan ........................................ 536/30
48-28648  9/1973  Japan ......................................... 536/3

OTHER PUBLICATIONS

Tomaru et al., "Bulletin of The Phytopath. Soc. Japan", vol. 39, p. 231, 1973.
Tomaru et al., "Bulletin of The Phytopath. Soc. Japan", vol. 41, No. 2, pp. 155–161, 1975.

*Primary Examiner*—Johnnie R. Brown
*Attorney, Agent, or Firm*—Stevens, Davis, Miller & Mosher

[57] ABSTRACT

A plant viral disease preventive composition contains an alginate, as active ingredient, having properties of:
(a) neutralization degree of 10 to 30%, said neutralization degree (wt %) being given from:

$$\frac{(C_5H_7O_4COOM)_m}{(C_5H_7O_4COOH)_{n-m} + (C_5H_7O_4COOM)_m} \times 100$$

where $(C_5H_7O_4COOH)_n$ is the molecular formula of the alginate, m is the number of the carboxylate groups in one molecule of the alginate, and M is an alkali metal or ammonium group; and/or
(b) viscosity in a 1 wt % aqueous solution at 20° C. is 2 to 10 centipoises.

13 Claims, No Drawings

PLANT VIRAL DISEASE PREVENTIVE ALGINATE CONTAINING COMPOSITIONS

DETAILED DESCRIPTION OF THE INVENTION

It is reported that various kinds of macromolecular substances derived from living bodies, such as alginic acid, casein, etc., have preventive effects on plant diseases, such as for example viral infection inhibitory effect, and particularly alginic acid is of use in the field of agricultural chemicals as a preventive against infection of plant viruses such as tobacco mosaic virus (TMV), cucumber mosaic virus (CMV), etc. (Bulletin of The Phytopathological Society of Japan, 39, 231, 41, 155–161, and Japanese Pat. No. 722,522 and No. 717,594).

However, alginic acid is incommodious in its treatment and use as it is insoluble in water. On the other hand, sodium alginate, although soluble in water, has extremely high affinity for water and extraordinarily high viscosity when wetted with water, so that it is extremely difficult to have it dissolved in water in a short time so that no "lumps" will be formed. Therefore, prolonged heating or stirring is required for dissolving these substances in water for practical application by way of spray to the plants. These substances also present the problems of insufficient effect, phytotoxicity to the plants and clogging of the sprayer because of their sluggishness in dissolving in water.

Various methods have been proposed for effecting quick dissolution of sodium alginate in water, such as addition of sugar, saline or such, previous wetting with alcohol, glycerin or the like, suspending of said substance in alcohol, propylene glycol or the like before dissolving in water, and coating with a poor soluble material previous to dissolution (Japanese Patent Pub. No. 7688/73). Nevertheless, none of these methods is able to attain the object to a satisfactory degree.

U.S. Pat. No. 3,891,756 discloses an agricultural chemical blend of carbonates, organic acids and silica for making the biopolymer substances such as alginic acid easily soluble in water.

The present inventors have made further studies with the object of making more easy and more effective the use of the plant viral disease preventive compositions containing alginic acid or its salts as active ingredient and found out that the solubility of the compositions is greatly affected by the ratio of the free carboxyl groups to carboxylate groups in the alginic acid molecules as well as the viscosity of the alginate used.

Thus, the present invention concerns the preparation of the plant viral disease preventives containing alginic acid or its salts as an active inpedient, characterizing the use of alginates having following properties (a) and/or (b):

(a) neutralization degree of 10 to 30% (the term "neutralization degree" is used here to mean the weight percent (wt%) of carboxylate in the alginic acid molecules), and (b) viscosity in a 1 wt% aqueous solution at 20° C. is 2 to 10 centipoises (cp).

This invention is also intended to provide the plant viral disease preventive compositions containing said types of alginate and further blended with an assistant composed of a carbonate and an organic acid, and/or a carrier containing silica, and/or a surface active agent, for further increasing the solubility and preventive effect of the compositions.

The present invention is now described in detail by starting with the discussion on the properties of alginic acid which is a base material of the compositions of this invention. Alginic acid, expressed by the general formula $(C_5H_7O_4COOH)_n$, is derived from polysaccharide contained richly in Phaeophyceae such as Ecklonia. This acid is a copolymer of D-mannuronic acid and L-gluronic acid, and its average polymerization degree (n) is considered to be of the order of 250 to 900. Alginic acid and alginate are distinguished from each other according to whether the carboxyl group of the pyranose ring that constitutes the skeleton structure is either a free acid type or a carboxylate type. Both alginic acid and alginates have extremely high affinity for water owing to hydrogen bonding of water to the carboxyl and hydroxyl groups in the pyranose ring, but alginic acid is insoluble in water whereas the sodium, potassium and ammonium salts of alginic acid are soluble in water and form a viscous solution.

We have directed our attention to such difference in properties between alginic acid and alginates and made researches into their water solubility by varying the amount (wt%) of the carboxylate groups relative to the total number of carboxylate and carboxyl groups of the pyranose ring constituting the skeleton of alginic acid. This weight ratio is termed "neutralization degree" in the specification revealed the fact that the alginates with neutralization degree of from 10 to 30% are quick to dissolve or disperse in water. It was further disclosed that use of the alginates with such low neutralization degree can provide the plant viral disease preventive compositions which are easy to use and high in effect.

We also gave attention to the relationship between the viscosity and solubility of the alginates.

We knew, from many tests, that when water is added to the agricultural chemical compositions prepared from various kinds of available sodium alginates, whose viscosity in a 1 wt% aqueous solution at 20° C. is 30 to 1,000 cp either singly or by blending a foam-forming assistant or assistants, the granule surface alone is impregnated with water and the undissolved lumps of particles are formed due to high water affinity and high viscosity of the alginate, but stiffness of such lumps is proportional to the viscosity of the alginate used. That is, in case of using an alginate with viscosity of 30 to 50 cp, the "lumps" formed in the process are not so strong but are easily broken down by about 15-minute agitation to produce a uniform solution. However, 15-minute agitation at the time of use is very inefficient and impractical.

We have further expanded the scope of study to the alginates with lower ranges of viscosity. The alginates with viscosity of lower than 30 cp, however, are far part from the standard quality and utility of those alginates which are generally considered available for practical use, and particularly those having viscosity of 2 to 10 cp in a 1 wt% aqueous solution at 20° C. are far lower in viscosity than the so-called standard alginates.

Since the alginates with viscosity of lower than 30 cp can not be synthesized according to the normal heat-depolymerization method we prepared the specimens of such alginates by first depolymerizing the material in the form of alginic acid to a desired degree of polymerization and then returning it to a salt type.

The results of the tests conducted on the thus synthesized hyper-low-viscosity alginate specimens by adding water thereto with or without blending a foam-forming assistant or assistants showed that although specimens with viscosity ranging from 30 to 10 cp form the "lumps" just like those with higher viscosity, the specimens with viscosity of lower than 10 cp are drastically improved in solubility. It was also found that a greater degree of improvement in solubility is provided in the specimens with a lower viscosity, but in view of the results of various biological tests of the plant viruses such as TMV and CMV, it is recommended to define the lower limit of viscosity to 2 cp, preferably 3 cp.

The preferred examples of the water-soluble alginates usable in this invention include sodium alginate, potassium alginate and ammonium alginate. Among such water-soluble alginates, those with the neutralization degree of 10 to 30%, preferably 10 to 20%, are actually used in the process of this invention.

The "neutralization degree" (%) as so termed in this invention is given by the following equation, assuming that m pieces of carboxyl groups in the alginic acid of the general formula $(C_5H_7O_4COOH)_n$ are of the salt type:

$$\text{Neutralization degree (\%)} = \frac{(C_5H_7O_4COOM)_m}{(C_5H_7O_4COOH)_{n-m} + (C_5H_7O_4COOM)_m} \times 100 \quad \text{(by weight ratio)}$$

(where M represents Na, K or $NH_4$).

The alginates with such range of neutralization degree may be obtained, for example, by dissolving a commercially available alginate (with high neutralization degree) in water, adding thereto a mineral acid and then methanol under agitation to deposit a gel, and when filtering out and drying such a gel.

In this invention, it is also possible to use the water-soluble alginates which, when adjusted to pH 5 to 7 at 20° C., have viscosities of 2 to 10 cp, instead of the alginates with the above-defined range of neutralization degree. In this case, the neutralization degree of the alginate used is not important.

Such low-viscosity alginates can not be produced by the depolymerization method by means of heating which is a routine practice for lowering viscosity. Therefore, for the preparation of such alginates, a commercially available alginate is treated with an acid to form alginic acid, followed by heating for depolymerization to lower the viscosity to a prescribed level, and the thus treated alginic acid is reconverted into an alginate.

The low-neutralization-degree or low-viscosity alginates according to this invention may be dissolved singly in water and immediately sprayed on the plants, but it is recommended to add a carbonate and an organic acid as an assistant for further increasing solubility of the compositions. Usually, the compositions are further mixed with a carrier, a surface active agent and the like and formulated into the forms convenient for use as agricultural chemicals. A preferred formulation is a wettable powder obtained by adding the above-mentioned assistant, a solid carrier and a surface active agent to the low-viscosity or low-neutralization-degree alginates.

Examples of the carbonates usable as a component of the assistant include calcium carbonate, sodium bicarbonate, sodium carbonate, potassium bicarbonate, potassium carbonate and ammonium carbonate. The organic acid used as another component of the assistant may be citric acid, succinic acid, fumaric acid, lactic acid, malic acid, maleic acid, phthalic acid, tartaric acid, acetic acid or a higher fatty acid such as lauric acid. The carbonate and organic acid react with each other in water to generate foams, causing dispersion of the alginate, to expedite its dissolution in water. For this purpose, said both materials may be used in equivalent quantities. However, in case of using an alginate with a low neutralization degree, the amount of the carbonate must be changed depending on the neutralization degree and quantity of the alginate used as the carbonate is reacted with the alginate and thereby consumed when dissolved in the water. The amount of carbonate is controlled so that a 1% aqueous solution of a plant viral disease preventive composition (the final product) will show no phytotoxicity to the plants. Usually, the sum of the carbonate and organic acid will be not greater than 35% by weight, preferably not greater than 25% by weight, based on the alginate.

In the present invention, the above-mentioned types of alginates, that form the principal constituent of the compositions, may be used in combination with various kinds of biopolymers which have preventive effects against plant viral infection, such as for example carrageenan, casein, α-globulin, β-globulin, lact-globulin, albumin, gluten, pectin, starch, gelatin, xylose, arabinose and salts thereof. The amount of these biopolymers blended should be less than 40% by weight, preferably less than 20% by weight, based on the alginate.

Silica or a silica-containing material is preferred for use as the carrier. More definitely, silica, clay minerals such as talc, clay, kaolin or bentonite, diatom earth, white carbon and the like are recommended. Such carrier is preferably used in an amount of 1 to 30% by weight (calculated in terms of $SiO_2$), based on the alginate.

It is also desirable to add a surface active agent to the compositions of this invention because addition of such surface active agent betters solubility of the composition and also increases the spreading effect of the composition when it is sprayed to the plants.

The surface active agent used in this invention may be selected from a wide range of generally available nonionic and anionic surfactants, but it is desirable that such surface active agent has high affinity for the biopolymers, excellent wettability and dispersibility and low toxicity. Preferred examples of such surface active agent are polyoxyethylenic nonionic surface active agents such as polyoxyethylene sorbitan monolaurate, polyoxyethylene sorbitan monooleate, polyoxyethylene sorbitan dioleate, polyoxyethylene sorbitan monostearate hexaoxyethylene nonyl phenyl sodium phosphate, tetraoxyethylene lautyl potassium phosphate or heptaoxyethylene oleil sodium phosphate, and the anionic surface active agents such as higher alcohol sulfates, and the amount of such surface active agent blended in the compositions of this invention should be within the range of 1 to 10% by weight, based on the alginate.

As described above, the alginates with neutralization degree of 10 to 30% or with low-viscosity used in the present invention, either when dissolved singly in water or when blended with a foaming assistant or other additives, are readily dissolved without forming "lumps."

When the ordinary alginates with high neutralization degrees are added into water whether singly or blended with said assistant, they are not perfectly dissolved and only the surface portions of the granules are brought into a water-impregnated condition, thus forming so-called "lumps," due to high affinity to the water of the alginate and its extraordinarily high viscosity shown when immersed in water.

On the other hand, the ordinary alginic acid with low neutralization degree is insoluble in water, so that when it is added into water, it settles down in water even if an alkaline source sufficient to neutralize the alginic acid is blended. Therefore, the neutralization reaction is retarded and 10- to 20-minute agitation is required for properly advancing the reaction. This is a fatal disadvantage for practical use although no "lumps" are formed.

The low-viscosity alginates according to this invention, cause no gelatinization or agglomeration which is often seen with the ordinary sodium alginate particularly when dissolved in hard water or mixed with other agricultural chemicals.

The method of application of the plant viral disease preventive compositions obtained according to this invention is not subject to any specific restriction. Any method commonly practiced for application of this kind of agricultural chemicals may be employed. The composition shown in Example 1, when applied for prevention of the TMV diseases of tobacco may be used in the following way. The composition is diluted 200 times with water and the solution is sprayed all over the tobacco seedlings at the rate of 15 to 30 liters per 10 m² immediately before transplantation. Thereafter, the solution is sprayed before first mulching, last mulching and bud cutting, respectively, in a volume of from 100 to 150 liters per 1000 m² depending on the size of the seedlings.

As the compositions of this invention can be easily and uniformly dissolved in water, they are easy to treat for application and no loss of the composition is suffered, ensuring good economy in practical use of the compositions.

The present invention is now described in further detail by way of examples of preparation of sodium alginate, examples of preparation of the compositions of this invention and tests, but this invention is not restricted by these examples but may be embodied in other forms without departing from the principle of the invention.

PREPARATION EXAMPLE 1

(preparation of sodium alginate with low neutralization degree)

Specimens of sodium alginate with diverse neutralization degrees were prepared in the following way.

A commercial product of sodium alginate (with neutralization degree of 88%) specified for use as food additive was dissolved in water to form a uniform solution and this solution was added with a predetermined quantity of dilute hydrochloric acid under violent agitation and then allowed to stand overnight at room temperature. Then a large amount of methanol was added and the deposited gel was filtered out, washed with methanol and dried in vacuo at a temperature of lower than 50° C.

In order to uniformalize the test conditions, the process was controlled such that each specimen would have the loss in weight on drying within the range of 7 to 15%.

The neutralization degree of each of the thus obtained specimens of sodium alginate was measured according to "Quantification of alkali salts of Organic Acids" in the Official Compendium of general test methods for food additives regulated by the Japanese law (the Food Sanitation Act).

There were thus prepared the specimens of sodium alginate with neutralization degrees of 51%, 29%, 20%, 15% and 10%, respectively. The loss in weight on drying (wt%) and viscosity (in a 1% aqueous solution with pH of 5 to 7 at 20° C.) of these specimens and of the commercial sodium alginate for food additive (two types with neutralization degree of 92% and 87%, respectively) and commercial alginic acid products (with neutralization degree of 5% and 4%, respectively) were measured, obtaining the results shown in Table 1 below.

TABLE 1

| Neutralization degree | wt% | 92 | 87 | 51 | 29 | 20 | 15 | 10 | 5 | 4 |
|---|---|---|---|---|---|---|---|---|---|---|
| Loss in weight on drying | wt% | 13.8 | 14.1 | 12.8 | 13.5 | 12.5 | 13.4 | 12.6 | 12.7 | 11.3 |
| Viscosity | cp | 120 | 53 | 115 | 112 | 116 | 47 | 110 | 107 | 57 |

PREPARATION EXAMPLE 2

(preparation of low-viscosity sodium alginate)

(1) 500 g of commercial alginic acid (with rotational viscosity of 62.0 cp adjusted to pH 7 in a 1% aqueous solution) were put into a kneader with a heater, and under agitation, 80 g of distilled water were further sprayed thereto. After depolymerization was carried out under agitation for 3 hours at 70° C., the thus treated alginic acid was added to 2.5 liters of distilled water and under violent agitation 20% NaOH aqueous solution was added to adjust it to pH 10 then continued agitation for 30 min. at room temperature. 10 liters of methanol were added to the obtained viscous aqueous solution to deposit sodium alginate in the form of gel, and the deposited gel was filtered out by a small size centrifugal filter. The thus obtained gel was sufficiently washed with 10 liters of methanol, then filtered out again by the centrifugal filter and dried under reduced pressure.

The dried gel was pulverized with a grinder and sieved with 80-mesh screen. Sodium alginate which passed through the 80-mesh screen had 11.7% loss in weight on drying (at 105° C.: for 4 hours) and 7.0 cp of rotational viscosity in a 1% aqueous solution at 20° C.

(2) 500 g of commercial sodium alginate (with a rotational viscosity of 80 cp) were dissolved in 10 liters of distilled water and were added gradually with about 300 ml of concentrated hydrochloric acid under violent agitation so as to deposit alginic acid in the form of gel. Thus deposited gel was filtered out by using a small size centrifugal filter. Further, by repeating sprinkle-washing and filtrating operations, there was obtained gelled alginic acid. The thus obtained gel was subjected to depolymerization in a kneader with a heater while agitating at 70° C. for 1 hour, then the deposited gel being treated in the same manner as described in the procedure (1). There was obtained sodium alginate with 12.3% loss in weight on drying and 3.0 cp of rotational viscosity in a 1% aqueous solution at 20° C. The specimens of sodium alginate with diverse viscosities prepared following to the above procedure (1) or (2) were shown in Table 2. In order to uniformalize the experimental conditions, the process was controlled such that the loss in weight upon drying will be within the range of 15 to 7% in all specimens.

TABLE 2

| Viscosity*1 | 220*2 | 80*3 | 25 | 10 | 7 | 5 | 3 | 2 | 1.5 |
|---|---|---|---|---|---|---|---|---|---|
| Neutralization degree (wt%) | Over 80 | Over 80 | Over 80 | Over 80 | 15 | Over 80 | Over 80 | Over 80 | Over 80 |
| Loss in weight an drying (wt%) | 13.1 | 12.8 | 12.5 | 13.4 | 11.8 | 12.9 | 13.2 | 11.7 | 11.1 |

(Notes)
*1: Viscosity in a 1 wt% aqueous solution at 20° C. was measured by using a rotary viscometer (Shibaura System Vismetron VSA-L).
*2, *3: Commercial sodium alginate for food additive

EXAMPLE 1

Specimens of sodium alginate with the neutralization degrees shown in Table 1, sodium caseinate, α-globulin, sodium bicarbonate, sodium carbonate, tartaric acid, malic acid, diatom earth, white carbon and Sorbon T-80 (polyoxyethylene sorbitan monooleate type surface active agent) were blended in the ratios (by weight) shown in Table 3 to obtain the corresponding compositions.

EXAMPLE 2

Specimens of sodium alginate specified in Table 2, sodium caseinate, α-globulin, sodium bicarbonate, sodium carbonate, tartaric acid, malic acid, diatom earth, white carbon and Sorbon T-80 were blended in the ratios (by weight) shown in Table 4 to obtain the corresponding compositions.

TABLE 3

| | | Sodium alginate Neutralization degree | | | | | | | | | Sodium caseinate | α-globulin | Sodium bicarbonate | Sodium carbonate | Tartaric acid | Malic acid | Diatom earth | White carbon | Surface active agent |
|---|---|---|---|---|---|---|---|---|---|---|---|---|---|---|---|---|---|---|---|
| | | 92 | 87 | 51 | 29 | 20 | 15 | 10 | 5 | 4 | | | | | | | | | |
| Compositions of this invention | 1-1 | | | 57 | | | | | | | 16 | | | 14.5 | | 6.5 | | 4 | 2 |
| | 1-2 | | | | 56 | | | | | | 16 | | | 15.5 | | 6.5 | | 4 | 2 |
| | 1-3 | | | | | 55 | | | | | 16 | | | 17 | | 6 | | 4 | 2 |
| | 1-4 | | | | | | 55 | | | | 16 | | | 17 | 6 | | | 4 | 2 |
| | 1-5 | | | | 70 | | | | | | | | 24 | | | | | 4 | 2 |
| | 1-6 | | | | | 70 | | | | | | | | 17 | | 6 | | 5 | 2 |
| | 1-7 | | | 57 | | | | | | | 16 | | | 14.5 | | 6.5 | 4 | | 2 |
| | 1-8 | | | | 56 | | | | | | | 16 | | 15.5 | | 6.5 | | 4 | 2 |
| | 1-9 | | | | 56 | | | | | | 16 | | | 15.5 | 6.5 | | | 4 | 2 |
| | 1-10 | | | | 56 | | | | | | 16 | | | 15.5 | | 6.5 | 4 | | 2 |
| | 1-11 | | | | | | 55 | | | | | 16 | | 17 | | 6 | | 4 | 2 |
| | 1-12 | | | | | | 55 | | | | 16 | | | 17 | 6 | | | 4 | 2 |
| | 1-13 | | | | | | 55 | | | | 16 | | | 17 | | 6 | 4 | | 2 |
| | 1-14 | | | | | 80 | | | | | | | | | | | | 16 | 4 |
| Comparative composition | 1-1 | 63 | | | | | | | | | 16 | | 8 | | 7 | | | 4 | 2 |
| | 1-2 | | 63 | | | | | | | | 16 | | 8 | | 7 | | | 4 | 2 |
| | 1-3 | | | 59 | | | | | | | 16 | | | 12 | 7 | | | 4 | 2 |
| | 1-4 | | | | | | | 55 | | | 16 | | | 17 | 6 | | | 4 | 2 |
| | 1-5 | | | | | | | | 55 | | 16 | | | 17 | | 6 | | 4 | 2 |

TABLE 4

| | | Sodium alginate Viscosity (cp) | | | | | | | | | Sodium caseinate | α-globulin | Sodium bicarbonate | Sodium carbonate | Tartaric acid | Malic acid | Diatom earth | White carbon | Surface active agent |
|---|---|---|---|---|---|---|---|---|---|---|---|---|---|---|---|---|---|---|---|
| | | 220 | 80 | 25 | 10 | 7 | 5 | 3 | 2 | 1.5 | | | | | | | | | |
| Compositions of this invention | 2-1 | | | 63 | | | | | | | 16 | | 8 | | 7 | | | 4 | 2 |
| | 2-2 | | | | 55 | | | | | | 16 | | | 17 | | 6 | | 4 | 2 |
| | 2-3 | | | | | 63 | | | | | 16 | | 8 | | 7 | | | 4 | 2 |
| | 2-4 | | | | | | 63 | | | | 16 | | 8 | | 7 | | | 4 | 2 |
| | 2-5 | | | | | | | 63 | | | 16 | | 8 | | 7 | | | 4 | 2 |
| | 2-6 | | 79 | | | | | | | | | | 8 | | 7 | | | 4 | 2 |
| | 2-7 | | | 71 | | | | | | | | | | 19 | 4 | | | 4 | 2 |
| | 2-8 | | | | 79 | | | | | | | | | | | | | 19 | 2 |
| | 2-9 | | | | | 79 | | | | | | | 8 | | | 7 | | 4 | 2 |
| | 2-10 | | | | | | 79 | | | | | | 8 | | | 7 | | 4 | 2 |
| | 2-11 | | | | 63 | | | | | | | 16 | 8 | | | 7 | | 4 | 2 |
| | 2-12 | | | | | | 63 | | | | 16 | | 8 | | 7 | | 4 | | 2 |
| | 2-13 | | | | | | | 63 | | | 16 | | 8 | | 7 | | 4 | | 2 |
| Comparative compositions | 2-1 | 63 | | | | | | | | | 16 | | 8 | | 7 | | | 4 | 2 |
| | 2-2 | | 63 | | | | | | | | 16 | | 8 | | 7 | | | 4 | 2 |
| | 2-3 | | | 63 | | | | | | | 16 | | 8 | | 7 | | | 4 | 2 |
| | 2-4 | 63 | | | | | | | | | | | 16 | 8 | | 7 | | 4 | 2 |
| | 2-5 | | | | | | | | | 63 | 16 | | 8 | | | 7 | | 4 | 2 |

TEST EXAMPLE 1

The potted tobacco seedlings (*Nicotiana glutinosa*) were sprayed with the 100-times, 200-times and 400-times diluted solutions of the compositions of Tables 3 and 4 (allowing 5-minute standing after dissolution in water) by a spray gun and then air-dried. Then a separately prepared purified tobacco mosaic virus (TMV) solution ($2 \times 10^{-7}$ g/ml) was inoculated into the seedlings according to the ordinary carborundum method and placed in a greenhouse for about 1 week to form the local lesions. For determining the TMV lesion inhibitory effect of the respective tested compositions, the number of the formed local lesions was examined and compared with those in the control section. The results are shown in Tables 5 and 6. It is evident that the compositions of this invention are superior in potency to the comparative compositions.

The purified TMV solution used in this test was prepared by separating and purifying TMV from the juice of the TMV infected leaves by using an ultracentrifuge.

Also shown in Tables 5 and 6 are the results of the test conducted by spraying the 100-times diluted solutions to the tobacco seedlings (Bright Yellow) to examine phytotoxicity.

TABLE 5

| Tested Compositions | | Preventive Value (%) | | | Phytotoxicity to tobacco seedlings (Bright Yellow) |
|---|---|---|---|---|---|
| | | Diluted 100 times | Diluted 200 times | Diluted 400 times | |
| Compositions of this invention | 1-1 | 98 | 98 | 94 | None |
| | 1-2 | 100 | 97 | 95 | None |
| | 1-3 | 99 | 97 | 94 | None |
| | 1-4 | 98 | 95 | 94 | None |
| | 1-5 | 96 | 94 | 93 | None |
| | 1-6 | 96 | 95 | 93 | None |
| | 1-7 | 97 | 96 | 92 | None |
| | 1-8 | 94 | 92 | 89 | None |
| | 1-9 | 97 | 96 | 93 | None |
| | 1-10 | 99 | 95 | 93 | None |
| | 1-11 | 95 | 92 | 88 | None |
| | 1-12 | 99 | 93 | 93 | None |
| | 1-13 | 97 | 95 | 94 | None |
| | 1-14 | 99 | 97 | 94 | None |
| Comparative compositions | 1-1 | 95 | 87 | 71 | None |
| | 1-2 | 94 | 88 | 72 | None |
| | 1-3 | 96 | 85 | 74 | None |
| | 1-4 | 93 | 83 | 70 | None |
| | 1-5 | 97 | 86 | 68 | None |
| Control | | 0 | | | |

Preventive value $= \left(1 - \dfrac{\text{number of lesions treated}}{\text{number of lesions untreated}}\right) \times 100$

TABLE 6

| | | Preventive Value (%) | | | Phytotoxicity to tobacco seedlings (Bright Yellow) |
|---|---|---|---|---|---|
| | | Diluted 100 times | Diluted 200 times | Diluted 400 times | |
| Compositions of this invention | 2-1 | 98 | 94 | 92 | None |
| | 2-2 | 97 | 95 | 94 | None |
| | 2-3 | 99 | 96 | 93 | None |
| | 2-4 | 97 | 94 | 91 | None |
| | 2-5 | 99 | 97 | 94 | None |
| | 2-6 | 95 | 94 | 93 | None |
| | 2-7 | 97 | 96 | 92 | None |
| | 2-8 | 96 | 93 | 91 | None |
| | 2-9 | 95 | 94 | 92 | None |
| | 2-10 | 94 | 92 | 89 | None |
| | 2-11 | 97 | 94 | 92 | None |
| | 2-12 | 98 | 95 | 92 | None |
| | 2-13 | 97 | 93 | 90 | None |
| Comparative compositions | 2-1 | 90 | 84 | 71 | None |
| | 2-2 | 93 | 85 | 77 | None |
| | 2-3 | 95 | 87 | 73 | None |
| | 2-4 | 91 | 86 | 75 | None |
| | 2-5 | 92 | 85 | 78 | None |
| Control | | 0 | | | |

TEST EXAMPLE 2

The preventive effect of the compositions of this invention against the cucumber mosaic virus (CMV) was tested according to the same method as in TEST EXAMPLE 1 but by using the cowpea seedlings (*Vigna sinensis var. sesquipendalis*, cv. Kurodanesanjaku). The results were as shown in Tables 7 and 8.

TABLE 7

| | | Preventive Valve (%) | | |
|---|---|---|---|---|
| | | Diluted 100 times | Diluted 200 times | Diluted 400 times |
| Compositions of this invention | 1-1 | 97 | 95 | 91 |
| | 1-2 | 99 | 96 | 93 |
| | 1-3 | 98 | 95 | 92 |
| | 1-4 | 95 | 94 | 90 |
| | 1-5 | 98 | 95 | 92 |
| | 1-6 | 96 | 94 | 91 |
| | 1-7 | 97 | 95 | 92 |
| | 1-8 | 94 | 91 | 86 |
| | 1-9 | 97 | 94 | 90 |
| | 1-10 | 99 | 96 | 95 |
| | 1-11 | 95 | 92 | 88 |
| | 1-12 | 93 | 93 | 91 |
| | 1-13 | 96 | 92 | 91 |
| | 1-14 | 98 | 96 | 92 |
| Comparative Compositions | 1-1 | 93 | 87 | 70 |
| | 1-2 | 94 | 85 | 71 |
| | 1-3 | 91 | 82 | 68 |
| | 1-4 | 95 | 89 | 72 |
| | 1-5 | 92 | 84 | 71 |
| Control | | 0 | | |

TABLE 8

| | | Preventive Value (%) | | |
|---|---|---|---|---|
| | | Diluted 100 times | Diluted 200 times | Diluted 400 times |
| Compositions of this invention | 2-1 | 95 | 93 | 91 |
| | 2-2 | 97 | 94 | 92 |
| | 2-3 | 99 | 96 | 92 |
| | 2-4 | 97 | 94 | 91 |
| | 2-5 | 97 | 93 | 90 |
| | 2-6 | 98 | 94 | 91 |
| | 2-7 | 95 | 92 | 89 |
| | 2-8 | 96 | 93 | 90 |
| | 2-9 | 96 | 91 | 88 |
| | 2-10 | 99 | 93 | 90 |
| | 2-11 | 95 | 91 | 89 |
| | 2-12 | 97 | 94 | 91 |
| | 2-13 | 98 | 95 | 92 |
| Comparative Compositions | 2-1 | 91 | 84 | 68 |
| | 2-2 | 92 | 82 | 73 |
| | 2-3 | 92 | 83 | 64 |
| | 2-4 | 90 | 80 | 72 |
| | 2-5 | 89 | 79 | 57 |
| Control | | 0 | | |

TEST EXAMPLE 3

A part of the compositioins shown in Tables 3 and 4 tested by using the potted tobacco seedlings (Bright Yellow and Xanthi). Each composition was diluted 200 times with water and, after 5-minute standing, sprayed all over tobacco seedlings by a spray gun. After air-drying of the sprayed chemicals, a purified TMV solution adjusted to TMV concentration of $2 \times 10^{-7}$ g/ml was inoculated into the 5×5 cm surface area of the largest leaf of each seedling. The assesment was made by counting, the number of the seedlings which developed the mosaic symptoms. The results are shown in Tables 9 and 10.

TABLE 9

| Species | Tested Compositions | | 7 days after inoculation | 14 days after inoculation | 21 days after inoculation |
|---|---|---|---|---|---|
| | | | Nr. of infected seadlings/ Nr. of inoculated seadlings | | |
| Bright Yellow | Compositions of this invention | 1-4 | 2/15 | 3/15 | 5/15 |
| | | 1-5 | 1/15 | 3/15 | 4/15 |
| | | 1-6 | 2/15 | 3/15 | 4/15 |
| | | 1-7 | 3/15 | 5/15 | 5/15 |
| | Comparative composition | 1-1 | 4/15 | 6/15 | 9/15 |
| | Control | | 5/10 | 10/10 | 10/10 |
| Xanthi | Compositions of this invention | 1-4 | 1/15 | 3/15 | 5/15 |
| | | 1-5 | 2/15 | 4/15 | 5/15 |
| | | 1-6 | 1/15 | 3/15 | 4/15 |
| | | 1-7 | 3/15 | 5/15 | 6/15 |
| | Comparative composition | 1-1 | 4/15 | 7/15 | 10/15 |
| | Control | | 4/10 | 10/10 | 10/10 |

TABLE 10

| Species | Tested compositions | | 7 days after inoculation | 14 days after inoculation | 21 days after inoculation |
|---|---|---|---|---|---|
| | | | Nr. of infected seadlings/ Nr. of inoculated seadlings | | |
| Bright Yellow | Compositions of this invention | 2-2 | 1/15 | 3/15 | 6/15 |
| | | 2-4 | 2/15 | 3/15 | 4/15 |
| | | 2-6 | 2/15 | 4/15 | 5/15 |
| | | 2-7 | 2/15 | 4/15 | 4/15 |
| | Comparative compositions | 2-1 | 4/15 | 7/15 | 11/15 |
| | | 2-5 | 3/15 | 10/15 | 12/15 |
| | Control | | 10/15 | 12/15 | 15/15 |
| Xanthi | Compositions of this invention | 2-2 | 2/15 | 4/15 | 5/15 |
| | | 2-4 | 1/15 | 3/15 | 5/15 |
| | | 2-6 | 1/15 | 4/15 | 4/15 |
| | | 2-7 | 2/15 | 3/15 | 5/15 |
| | Comparative compositions | 2-1 | 4/15 | 9/15 | 11/15 |
| | | 2-5 | 3/15 | 9/15 | 12/15 |
| | Control | | 11/15 | 13/15 | 15/15 |

TEST EXAMPLE 4

The solubility in water of the compositions of this invention was tested. 20 gr of each composition was put into a 3-liter beaker containing 2 liters of service water and, after 2-minute standing (under a condition ready to form "lumps"), the solution was agitated and its condition one minute thereafter was examined. Also, the time required for each composition to get perfectly dissolved to form a lucid solution free of lumps was measured. The results are shown in Tables 11 and 12.

TABLE 11

| Tested compositions | | Condition after one-minute agitation | Time till perfect dis-solution of composition |
|---|---|---|---|
| Compositions of this invention | 1-1 | B | 1 min. 30 sec. |
| | 1-2 | A | within 1 min. |
| | 1-3 | A | within 1 min. |
| | 1-4 | A | within 1 min. |
| | 1-5 | A | within 1 min. |
| | 1-6 | A | within 1 min. |
| | 1-7 | A | within 1 min. |
| | 1-8 | B | 1 min. 30 sec. |
| | 1-9 | A | within 1 min. |
| | 1-10 | A | within 1 min. |
| | 1-11 | B | 1 min. 30 sec. |
| | 1-12 | A | within 1 min. |
| | 1-13 | A | within 1 min. |
| | 1-14 | E | — |
| Comparative compositions | 1-1 | D | more than 30 min. |
| | 1-2 | D | more than 30 min. |
| | 1-3 | D | 15 min. |
| | 1-4 | C | 15 min. |
| | 1-5 | C | 15 min. |

TABLE 12

| Tested compositions | | Condition after 30-second agitation | Time till perfect dissolution of composition |
|---|---|---|---|
| Compositions of this invention | 2-1 | B | within 1 min. |
| | 2-2 | A | within 30 sec. |
| | 2-3 | A | within 30 sec. |
| | 2-4 | A | within 30 sec. |
| | 2-5 | A | within 30 sec. |
| | 2-6 | B | within 1 min. |
| | 2-7 | A | within 30 sec. |
| | 2-8 | A | within 30 sec. |
| | 2-9 | A | within 30 sec. |
| | 2-10 | A | within 30 sec. |
| | 2-11 | B | within 1 min. |
| | 2-12 | A | within 30 sec. |
| | 2-13 | A | within 30 sec. |
| Comparative compositions | 2-1 | D | more than 30 min. |
| | 2-2 | D | more than 30 min. |
| | 2-3 | B-D | 15 min. |
| | 2-4 | D | more than 30 min. |
| | 2-5 | A | within 30 sec. |

Rating:
A: perfectly dissolved
B: some "lumps" remained
C: some insolubles remained
D: most part remained as lumps
E: perfectly dispersed

TEST EXAMPLE 5

The change of solution viscosity with variation of hardness of diluting water was examined. 1 gr of each composition of this invention was diluted with 200 ml of hard water with various hardnesses and, after 30-minute agitation, the solution viscosity was measured at 20° C. by a rotary viscometer (Vismetron VSA-L by Shibaura System Ltd.). Spreadability of each solution was also examined by using a knapsack type sprayer (MA-10 by Yokohama Ueki Co., Ltd.). The results are shown in Table 13.

TABLE 13

| | | Hardness of diluting water (DH value)* | | | | | | | |
|---|---|---|---|---|---|---|---|---|---|
| | | 0 | 5 | 10 | 12 | 14 | 16 | 18 | 20 |
| Compositions of this invention | 2-2 | 3 (A)** | 3.2 (A) | 3.5 (A) | 4 (A) | 6 (A) | 10 (A) | 9 (A) | 7 (A) |
| | 2-4 | 2.2 (A) | 2.3 (A) | 2.4 (A) | 2.6 (A) | 3.0 (A) | 3.5 (A) | 3.4 (A) | 3.0 (A) |
| | 2-6 | 4 (A) | 4.5 (A) | 5 (A) | 8 (A) | 15 (A) | 19 (B)** | 16 (B) | 15 (A) |
| Com- | | | | | | | | | |

TABLE 13-continued

| | | Hardness of diluting water (DH value)* | | | | | | |
|---|---|---|---|---|---|---|---|---|
| | | 0 | 5 | 10 | 12 | 14 | 16 | 18 | 20 |
| parative Comparative | 2-1 | 22 (B) | 23 (B) | 40 (B) | 75 (C)** | 370 (D)** | 900 (D) | 850 (D) | 600 (D) |
| Compositions | 2-3 | 8 (A) | 9 (A) | 18 (B) | 29 (B) | 55 (C) | 90 (C) | 75 (C) | 60 (C) |

Upper row: viscosity (cp)
Lower row: spreadability**
(Notes)
*:German Hardness. 1 DH is equivalent to 17.85714 ppm of $CaCO_3$.
**:Rating of spreadability
(A): Excellent
(B): Slightly bad
(C): Bad
(D): Unspreadable

TEST EXAMPLE 6

2 gr of each of the compositions of this invention shown in Table 3 and predetermined quantities of commercial agricultural chemicals were weighed and diluted with 200 ml of service water and, after 5-minute agitation, the solution was examined to see whether it caused gelatinization and agglomeration. The results are shown in Table 14.

TABLE 14

| Mixed chemicals and thier weight | Compositions of this invention | | | Comparative compositions | |
|---|---|---|---|---|---|
| | 2-2 | 2-4 | 2-6 | 2-1 | 2-3 |
| Commercial product 1 0.5 g | A | A | A | D | C |
| Commercial product 2 0.2 g | A | A | A | B | B |
| Commercial product 3 0.2 g | A | A | A | A | A |
| Commercial product 4 0.4 g | A | A | B | D | D |
| Commercial product 5 0.2 g | A | A | A | C | C |
| Commercial product 6 0.2 g | A | B | A | D | D |
| Commercial product 7 0.1 g | A | A | A | C | C |
| Commercial product 8 0.2 g | A | A | A | B | A |
| Commercial product 9 0.2 g | A | A | A | D | D |
| Commercial product 10 0.4 g | B | B | C | D | D |

Rating:
A: No gelatinization and agglomeration.
B: Slightly gelatinized and agglomerated.
C: Considerably gelatinized and agglomerated.
D: Excessively gelatinized and agglomerated.

The commercial products (1 to 10) used in the test were the agricultural chemicals based by the following compounds.

Commercial product 1: zinc ethylene-bis(dithiocarbamate) (72%)
Commercial product 2: 1,2-bis(3-methoxycarbonyl-2-thioureido)benzene (70%, WP)
Commercial product 3: dimethyldicarbetoxyethyl.dithiophosphate (50%, EC)
Commercial product 4: Ethyldimethyldithiophosphorylphenyl acetate (50%, EC)
Commercial product 5: dimethyl(3-methyl-4-nitrophenyl)thiophosphate (50%, EC)
Commercial product 6: 0,0-diethyl-0-3,5,6-trichloro-2-pyridine phosphothioate (40%, EC)
Commercial product 7: methyl-1-(butylcarbamoyl)-2-benzimidazole carbamate (50%, WP)
Commercial product 8: S-methyl-N-[(methylcarbamoyl)oxy]thioacetimidate (45%, WP)
Commercial product 9: streptomycin sulfate (20%, WP)
Commercial product 10: cupric hydroxide (83%, WP)

The concentration of active ingredient and formulation type is shown in parentheses. WP means wettable powder, and EC means emulsifiable concentrate.

What is claimed is:

1. A plant viral disease preventive composition comprising:
an alginate having the following properties (a) and (b):
(a) a neutralization degree of 10 to 30%, said neutralization degree (wt%) being given from:

$$\frac{(C_5H_7O_4COOM)_m}{(C_5H_7O_4COOH)_{n-m} + (C_5H_7O_4COOM)_m} \times 100$$

wherein m is the number of the carboxylate groups substituted with an alkali metal or ammonium group M;
(b) a viscosity in a 1 wt% aqueous solution at 20° C. of 2 to 10 centipoises;
at least one biopolymer selected from the group consisting of casein, its water-soluble salts and globulin, said biopolymer being blended in an amount of 0 to 40% by weight based on the alginate;
a carbonate and an organic acid, the sum of said carbonate and organic acid being 0 to 35% by weight based on the alginate;
a solid carrier containing silica, said carrier being in an amount of 1 to 30% by weight based on the alginate; and
a surface active agent in an amount of 1 to 10% by weight based on alginate.

2. A plant viral disease preventive composition comprising:
(1) as the active ingredient, an alginate having at least one of the following properties (a) and (b):
(a) a neutralization degree of 10 to 30%, said neutralization degree (wt%) being given from:

$$\frac{(C_5H_7O_4COOM)_m}{(C_5H_7O_4COOH)_{n-m} + (C_5H_7O_4COOM)_m} \times 100$$

wherein m is the number of the carboxylate groups substituted with an alkali metal or ammonium group M;
(b) a viscosity in a 1 wt% aqueous solution at 20° C. of 2 to 10 centipoises; and
(2) at least one member selected from the group consisting of:
I. A carbonate and an organic acid;
II. silica-containing carriers; and
III. surface active agents.

3. A composition according to claim 2, wherein the alginate is selected from the sodium, potassium and ammonium salts of alginic acid.

4. A composition according to claim 2, comprising a carbonate, an organic acid and a biopolymer having a plant viral infection preventive effect other than the alginates.

5. A composition according to claim 2, comprising a carbonate, an organic acid, a biopolymer having a plant viral infection preventive effect other than the alginates, a carrier containing silica, and a surface active agent.

6. A composition according to claim 2, wherein an alginate with neutralization degree of 10 to 30% is used as the alginate component.

7. A composition according to claim 2, wherein an alginate whose viscosity in a 1% aqueous solution at 20° C. is 2 to 10 centipoises is used as the alginate component.

8. A plant viral disease preventive composition comprising:
(a) an alginate whose viscosity in a 1% aqueous solution at 20° C. is 2 to 10 centipoises;
(b) at least one kind of biopolymer selected from casein, its water-soluble salts and globulin, said biopolymer being used in an amount of 0 to 40% by weight based on the alginate;
(c) a carbonate and an organic acid, the sum of said carbonate and organic acid being 0 to 35% by weight based on the alginate
(d) a solid carrier containing silica, said carrier being in an amount of 1 to 30% by weight based on the alginate; and
(e) a surface active agent in an amount of 1 to 10% by weight based on the alginate.

9. A method for controlling plant viral disease which comprises treating the plants affected by a viral disease with the preventive composition of claim 2.

10. The composition of claim 4 wherein said carbonate is an inorganic carbonate selected from the group consisting of calcium carbonate, sodium bicarbonate, sodium carbonate, potassium bicarbonate, potassium carbonate and ammonium carbonate; and said organic acid is selected from the group consisting of citric acid, succinic acid, fumaric acid, lactic acid, malic acid, maleic acid, phthalic acid, tartaric acid, acetic acid, and higher fatty acids.

11. The composition of claim 4 wherein said biopolymer is selected from the group consisting of carrageenan, casein, alpha-globulin, beta-globulin, lact-globulin, albumin, gluten, pectin, starch, gelatin, xylose, arabinose and salts thereof.

12. The composition of claim 1 wherein said carbonate is an organic carbonate selected from the group consisting of calcium carbonate, sodium bicarbonate, sodium carbonate, potassium bicarbonate, potassium carbonate and ammonium carbonate; said organic acid is selected from the group consisting of citric acid, succinic acid, fumaric acid, lactic acid, malic acid, maleic acid, phthalic acid, tartaric acid, acetic acid, and higher fatty acids; and wherein said biopolymer is selected from the group consisting of carrageenan, casein, alpha-globulin, beta-globulin, lact-globulin, albumin, gluten, pectin, starch, gelatin, xylose, arabinose and salts thereof.

13. The composition of claim 8 wherein said carbonate is an inorganic carbonate selected from the group consisting of calcium carbonate, sodium bicarbonate, sodium carbonate, potassium bicarbonate, potassium carbonate and ammonium carbonate; said organic acid is selected from the group consisting of citric acid, succinic acid, fumaric acid, lactic acid, malic acid, maleic acid, phthalic acid, tartaric acid, acetic acid, and higher fatty acids; and wherein said biopolymer is selected from the group consisting of carrageenan, casein, alpha-globulin, beta-globulin, lact-globulin, albumin, gluten, pectin, starch, gelatin, xylose, arabinose and salts thereof.

* * * * *